United States Patent [19]

Kellan

[11] Patent Number: 5,370,652
[45] Date of Patent: Dec. 6, 1994

[54] SURGICAL KNIFE BLADE FOR MAKING SUTURELESS INCISIONS IN THE EYE AND METHODS THEREFOR

[76] Inventor: Robert E. Kellan, 60 East St., Suite 1100, Methuen, Mass. 01844

[21] Appl. No.: 958,259

[22] Filed: Oct. 8, 1992

[51] Int. Cl.$^5$ .............................................. A61F 9/00
[52] U.S. Cl. .................................. 606/166; 606/172; 30/294; 33/512
[58] Field of Search ............... 606/166, 170, 172, 167; 30/294, 123.7, 289, 41.7, 41.8, 123, 320; 33/512, 836

[56] References Cited

U.S. PATENT DOCUMENTS

| | | | |
|---|---|---|---|
| 140,336 | 4/1873 | Alexander . | |
| 307,767 | 11/1884 | Heysinger | 30/320 |
| 354,800 | 12/1886 | McDonald . | |
| 742,373 | 10/1903 | Alden | 30/123 |
| 3,543,401 | 12/1970 | Scott et al. | 30/294 |
| 4,163,317 | 8/1979 | Levanti | 30/123.7 |
| 4,319,564 | 3/1982 | Karickhoff | 33/512 |
| 4,337,773 | 7/1982 | Raftopoulos et al. . | |
| 4,340,059 | 7/1982 | Marinoff . | |
| 4,552,146 | 11/1985 | Jensen et al. | 606/172 |
| 4,884,569 | 12/1989 | Fedorov et al. . | |
| 5,012,818 | 5/1991 | Joishy | 128/754 |
| 5,098,438 | 3/1992 | Siepser | 606/107 |
| 5,109,869 | 5/1992 | Buckley | 33/512 |
| 5,217,476 | 6/1993 | Wishinsky | 606/167 |
| 5,224,950 | 7/1993 | Prywes | 606/166 |

FOREIGN PATENT DOCUMENTS

| | | | |
|---|---|---|---|
| 759941 | 10/1956 | United Kingdom . | |
| 1560143 | 4/1990 | U.S.S.R. | 606/167 |

OTHER PUBLICATIONS

"The Surgical Armamentarium", Amer. Hospital Supply Corp., American V. Mueller, pp. 2–9, 1980.

*Primary Examiner*—Tamara L. Graysay

[57] ABSTRACT

A surgical knife blade includes a cutting blade for penetrating tissue of the eye. First indicia is carried on the cutting blade proximally spaced from a tip thereof for being aligned with an external surface of the tissue when the cutting blade is inserted tip first in the tissue to form an initial incision having a depth equal to the distance that the first indicia is spaced proximally from the tip. The cutting edge is configured to form a subsurface tunnel within the thickness of the tissue when the cutting blade is moved from the initial incision along a plane transverse to the plane of the initial incision. Second indicia is carried on the blade proximally spaced from the tip for being aligned relative to the initial incision to gauge the length of the subsurface tunnel. A method of making sutureless incisions in the eye includes the steps of inserting the knife blade in the tissue along a plane transverse to the tissue to form the initial incision, aligning the first indicia with the external surface to obtain a depth for the initial incision equal to the distance that the first indicia is spaced from the tip, moving the knife blade from the initial incision along a plane transverse to a plane of the initial incision to form the subsurface tunnel, aligning the second indicia relative to the initial incision to gauge the length of the tunnel and making a second incision from the tunnel through the tissue along a plane transverse to the plane of the tunnel.

12 Claims, 7 Drawing Sheets

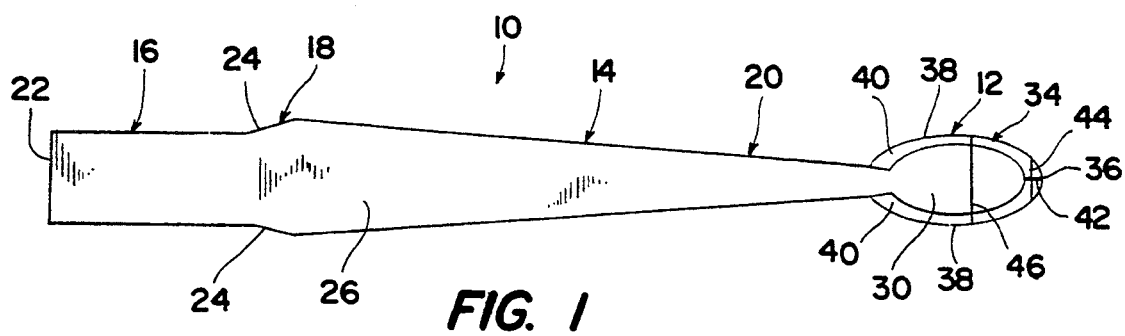
FIG. 1
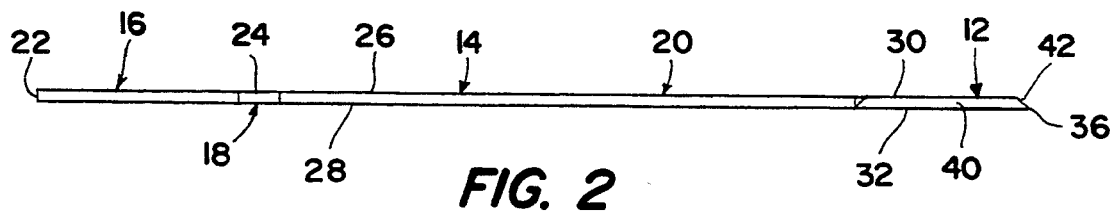
FIG. 2
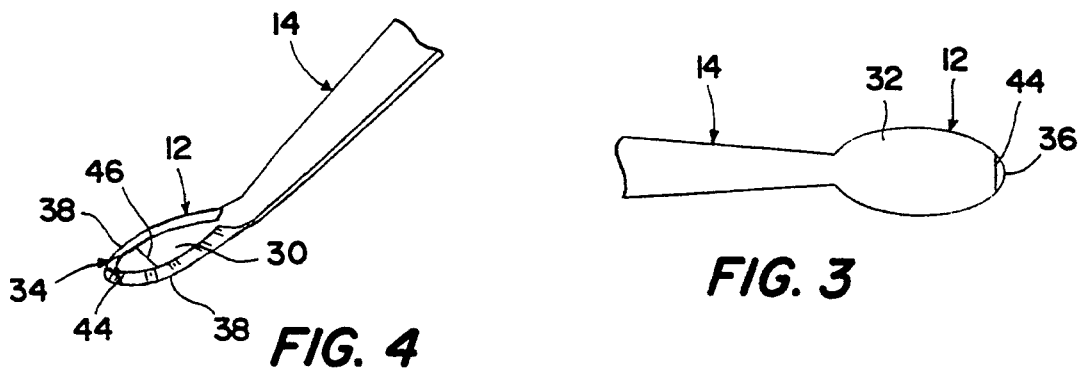
FIG. 4
FIG. 3

SURGICAL KNIFE BLADE FOR MAKING SUTURELESS INCISIONS IN THE EYE AND METHODS THEREFOR

BACKGROUND OF THE INVENTION

1. Field of the Invention

The present invention pertains to eye surgery and, in particular, cataract: surgery and surgical knife blades and methods for making sutureless incisions in the eye.

2. Description of the Prior Art

Various surgical procedures of the eye require that incisions be made in the eye to gain access to the anterior chamber as well as other parts of t-he eye. In cataract surgery, an incision is made in the eye to gain access to a cataractous natural lens allowing removal of the cataractous lens and implantation of an intraocular lens implant. One popular technique, i.e. the extracapsular technique, for cataract surgery involves making a plunge cut or one plane incision through the scleral corneal junction of the eye to enter the anterior chamber allowing an instrument, such as a phacoemulsifier, for removing the cataractous lens to be introduced at the anterior chamber through the incision. Once the cataractous lens has been removed with the instrument, an intraocular lens implant is inserted through the incision, which is enlarged as necessary to receive the implant, and guided into the position previously occupied by the natural lens. Upon implantation of the intraocular lens implant, the incision is closed with sutures. Suturing the corneal incision can be very tedious and time consuming due to the extremely small size of the sutures, and the sutures increase the occurrence of post-operative astigmatism, patient discomfort and foreign body sensation as well as other complications of surgery.

Sutureless incisions, also known as corneal valve incisions, represent a latest significant advance in intraocular surgery and, in particular, cataract surgery. Sutureless incisions, wherein the positive pressure of the eye maintains the incisions closed and the tissue approximated for healing without the need for sutures, has numerous advantages over incisions requiring suture closure including reduction of post-operative astigmatism, better maintenance of the anterior chamber, avoidance of foreign body sensation, enhanced comfort through the post-operative period and simplification of surgical procedures of the eye. U.S. Pat. No. 5,098,438 to Siepser is illustrative of surgical knife blades and methods for making sutureless incisions in intraocular surgery. One drawback of prior art surgical knife blades and methods for making sutureless incisions in the eye is that separate knife blades must be utilized to form an initial incision and a subsurface pocket, respectively. Another drawback of prior art surgical knife blades and methods for forming sutureless incisions in the eye is that there is no way to gauge the optimal distance from an anatomical reference for the site of the initial incision. Additionally, prior art surgical knife blades and methods of making sutureless incisions in the eye do not allow the extent of commitment into the sclera and clear cornea to be precisely judged prior to entering the anterior chamber such that the subsurface pocket cannot be controllably extended into the cornea to allow the anterior chamber to be entered therefrom. A further disadvantage of prior art surgical knife blades and methods of making sutureless incisions in the eye is that the subsurface pocket cannot be made in its entirety in the cornea, where indicated, allowing the initial incision to be made at the limbus.

SUMMARY OF THE INVENTION

Accordingly, it is a primary object of the present invention to overcome the above-mentioned disadvantages of prior art surgical knife blades and methods for making sutureless incisions in the eye.

Another object of the present invention is to provide a single surgical knife blade for making both an initial plunge cut incision and a subsurface tunnel incision extending from the initial incision in tissue of the eye allowing the anterior chamber to be entered from the subsurface tunnel.

An additional object of the present invention is to provide a surgical knife blade having an indicia marking carried thereon for being aligned with an external surface of tissue of the eye to form an initial plunge cut incision of a corneal valve incision in the tissue to an optimal depth.

It is also an object of the present invention to provide a surgical knife blade having an indicia marking thereon proximally spaced 0.3 mm from a distal tip of the blade for precisely forming a 0.3 mm deep initial plunge cut incision when the blade is inserted tip first in tissue of the eye and the indicia marking is aligned with an external surface of the tissue.

Yet another object of the present invention is to provide a surgical knife blade having a gauge marking carried thereon spaced from a distal tip of the blade a distance equal to the optimal distance from an anatomical reference on the eye to the site for an initial incision to be made with the blade in tissue of the eye allowing the site to be identified on the tissue with the tip aligned with the anatomical reference.

A further object of the present invention is to provide a surgical knife blade having a gauge marking carried thereon 3.0 mm from a distal tip of the blade allowing the tip to be aligned with the anterior arcade of vessels of the eye and the gauge marking used to establish a site for an initial incision to be made in tissue of the eye and approximately 1.5 mm into clear cornea to achieve an overall incision length of 3.0 mm.

The present invention has as an additional object to provide a surgical knife blade having a gauge marking carried thereon for being disposed relative to an initial plunge cut incision made with the blade in tissue of the eye to gauge the length of a subsurface tunnel formed with the blade to extend from the initial incision.

It is also an object of the present invention to provide a surgical knife blade having a gauge marking carried thereon for judging the extent of commitment of the blade into the cornea of the eye when forming a subsurface tunnel of a corneal valve incision to extend into the cornea.

Still another object of the present invention is to provide a method of making sutureless incisions in the eye including the steps of inserting a knife blade in tissue of the eye along a plane transverse to the tissue and aligning first indicia on the knife blade with an external surface of the tissue to obtain an optimal depth for the initial incision and a subsurface tunnel to be extended from the initial incision.

An additional object of the present invention is to provide a method of making sutureless incisions in the eye including the steps of aligning second indicia on the knife blade relative to an initial plunge cut incision formed with the blade in tissue of the eye to gauge the length of a subsurface tunnel formed with the blade in the tissue to extend from the initial incision transverse thereto.

It is also an object of the present invention to provide a method of making a corneal valve incision in the eye including the step of forming an initial plunge cut incision of the corneal valve incision at the limbus of the eye such that a subsurface tunnel extending from the initial incision is disposed entirely within the cornea.

Accordingly, these and other objects, benefits and advantages are realized with the present invention as characterized in a surgical knife blade having first indicia in the nature of markings or alignment lines carried thereon for being aligned with an external surface of tissue of the eye when the blade is inserted in the tissue along a plane transverse to the tissue in the manner of a plunge cut to form an initial incision. The alignment lines are disposed on anterior and posterior surfaces of the blade to be aligned with an external surface of the tissue and are proximally spaced from a tip of the blade a distance equal to an optimal depth, less than the thickness of the tissue, for the initial incision. Second indicia in the nature of a gauge marking or line carried on the blade is spaced proximally from the tip a distance equal to the distance from an anatomical reference on the eye to an optimal site for the initial incision such that the optimal site on the tissue can be identified with the tip aligned with the anatomical reference- The blade includes a cutting edge for making the initial plunge cut incision and a subsurface tunnel incision through the thickness of the tissue when the blade is moved through the tissue from the initial .incision along a plane transverse to the plane of the initial incision. The gauge line can be aligned relative to the initial incision to judge the length of the subsurface tunnel from the initial incision and the extent of commitment of the blade into clear cornea when forming the subsurface tunnel. A method of making sutureless incisions in the eye according to the present invention includes the steps of inserting the knife blade in the tissue along the plane transverse to the tissue to form the initial incision, aligning the first indicia with the external surface of the tissue, moving the knife blade from the initial incision along the plane transverse to the plane of the initial incision to form the subsurface tunnel within the thickness of the tissue, aligning the second indicia relative to the initial incision to gauge the length of the tunnel and making a second incision from the tunnel through the tissue along a plane transverse to the plane of the tunnel to penetrate through the thickness of the tissue and enter the anterior chamber of the eye.

The above and still further objects, features and advantages of the present invention will become apparent upon consideration of the detailed description set forth below, particularly when taken in conjunction with the accompanying drawings wherein like reference numerals in the various figures are utilized to describe like components.

BRIEF DESCRIPTION OF THE DRAWINGS

FIG. 1 is a top, plan view of a surgical knife blade according to the present invention.

FIG. 2 is a side view of the surgical knife blade of FIG. 1.

FIG. 3 is a broken bottom view of the surgical knife blade of FIG. 1.

FIG. 4 is a broken perspective view of a modification of the surgical knife blade according to the present invention.

DESCRIPTION OF THE PREFERRED EMBODIMENTS

Figure 9:
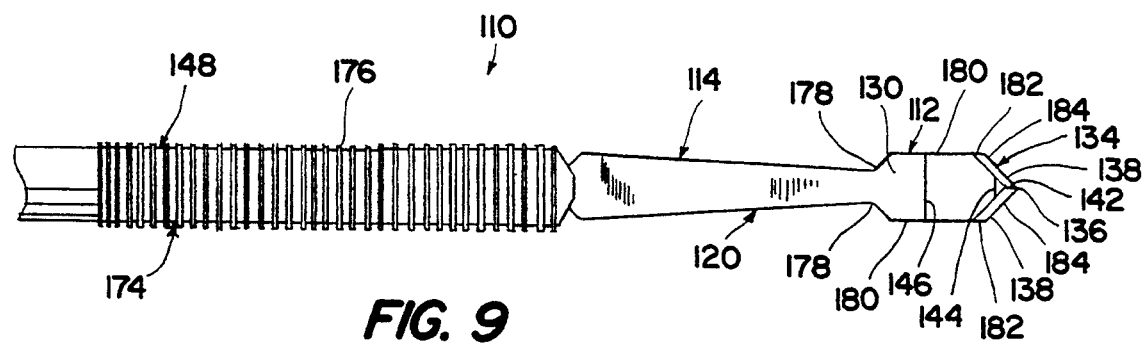
FIG. 9 is a top plan view of another modification of a surgical knife blade according to the present invention.

A surgical knife blade according to the present invention is illustrated at 10 in FIG. 1 and includes a cutting blade 12 and a shank 14 mounting the cutting blade 12. Shank 14 includes an elongate body made up of an end section 16, an intermediate section 18 and a forward section 20. End section 16 is of generally uniform width and terminates proximally at an end surface 22 and distally at opposing flared shoulders 24 of intermediate section 18. Intermediate section 18 extends distally from end section 16 with shoulders 24 terminating at forward section 20. Forward section 20 is tapered in a distal direction from shoulders 24 and terminates distally at cutting blade 12. As best illustrated in FIG. 2, shank 14 has an anterior surface 26 and a posterior surface 28 with a thickness defined therebetween, the anterior and posterior surfaces 26 and 28 being mirror images of each other to define a desired configuration for shank 14. The shank can have any desired configuration to be mounted on a handle, such as handle 148 illustrated in FIG. 9, coaxially secured to end section 16 allowing the handle to be grasped by a surgeon to manipulate blade 12. As shown in FIGS. 1 and 2, the anterior and posterior surfaces 26 and 28 of shank 14 are parallel to define a uniform minimal thickness, end section 16 has a rectangular surface configuration and forward section 20 has an elongate, truncated triangular surface configuration with intermediate section 18 being configured as a transition area smoothly joining the end and forward sections.

Blade 12 includes an anterior surface 30, a posterior surface 32 and a peripheral cutting edge 34 having a distalmost tip or point 36. Cutting edge 34 can have any desired configuration to form a plunge cut incision and a subsurface tunnel in tissue of the eye and, as illustrated in FIG. 1, cutting edge 34 is continuously curving to define an oval or elliptical configuration broken at forward section 20. Cutting edge 34 is made up of opposing, lateral cutting edge segments 38 extending distally from forward section 20 to meet at tip 36. The anterior and posterior surfaces 30 and 32 of blade 12 can be parallel as illustrated in FIG. 2 or non-parallel with a minimal thickness therebetween facilitating penetration of tissue and formation of a narrow width incision. Anterior surface 30 is beveled or angled along the lateral cutting edge segments 38 to define a sharp edge with the bevels or angles 40 for cutting edge segments 38 meeting at a ridge 42 aligned with tip 36. The maximum linear distance between the lateral cutting edge segments 38 measured transverse or perpendicular to a longitudinal axis of the blade defines a maximum width for the blade, and the width of the blade tapers from the maximum width to the tip 36. The cutting edge segments 38 can be symmetrical with the longitudinal axis of the blade with tip 36 and ridge 42 aligned with the axis as illustrated in FIG. 1, or the cutting edge segments can be non-symmetrical with the axis. The longitudinal axis of blade 12 can be coaxially aligned with a longitudinal axis of shank 14 as illustrated in FIGS. 1 and 2 to allow the blade to be axially aligned with the handle, or the blade longitudinal axis can be angularly offset from the shank longitudinal axis as illustrated in FIG. 4 to allow the blade to be angularly offset from the handle. The anterior and posterior surfaces 30 and 32 of blade 12 can be continuous with the anterior and posterior surfaces 26 and 28, respectively, of shank 14; and, where the longitudinal axis of the blade is aligned with the longitudinal axis of the shank, the anterior and posterior surfaces 30 and 32 can be coplanar with the anterior and posterior surfaces 26 and 28, respectively, as illustrated in FIG. 2.

Indicia in the nature of alignment lines 44 are disposed on the anterior and posterior surfaces 30 and 32 of blade 12 to be proximally spaced from tip 36 with each of the alignment lines 44 being disposed the same linear distance from tip 36, such distance being measured transverse or perpendicular to the alignment lines. The distance that alignment lines 44 are proximally spaced from tip 36 is equal to the desired depth of an incision made when the blade is inserted in tissue, such as the sclera, of the eye in a direction transverse or normal to the tissue in the manner of a plunge cut. Alignment lines 44 extend across the anterior and posterior surfaces 30 and 32 transverse to the longitudinal axis of the blade such that opposing ends of lines 44 are disposed along or adjacent opposing portions of cutting edge segments 38, the opposing ends of the alignment lines being disposed along the cutting edge segments in FIGS. 1 and 3. Depending on the size of the bevels or angles for cutting edge segments 38 and the desired depth for the incision, the line 44 on anterior surface 30 can be disposed along the bevels or angles 40 as shown in FIGS. 1 and 4. Indicia in the nature of a gauge line 46 is disposed on the anterior surface 30 to be proximally spaced from tip 36. Gauge line 46 is spaced from tip 36 by a linear distance, measured transverse or perpendicular to the gauge line 46, that is equal to an optimal distance from an anatomical reference, such as the anterior arcade of vessels of the eye, to the site or location for an incision to be made with the blade in the eye, and the distance that gauge line 46 is spaced from tip 36 provides a gauge for judging the length of a subsurface tunnel formed with the blade and the extent of commitment into clear cornea when forming a corneal valve incision as will be explained further below. Gauge line 46 extends across anterior surface 30 transverse to the longitudinal axis of blade 12 with opposing ends of gauge line 46 disposed along or adjacent opposing portions of cutting edge segments 38, the opposing ends of the gauge line being disposed along the cutting edge segments in FIG. 1. The opposing ends of gauge line 46 can be disposed inwardly of opposing portions of cutting edge segments 38 to be disposed along the non-beveled part of anterior surface 30 as illustrated in FIG. 4.

Blade 12 can be made from any material, such as stainless steel, suitable to be inserted in the body and can be made in many ways including from blanks obtained by various processes such as mechanical punching, cutting, electrical burning and photo-chemical machining. In addition to beveling or angling, the cutting edge 34 can be formed on blade 12 in many various ways including grinding. Shank 14 can be made of any suitable medical grade material, such as stainless steel, and can be fabricated in many ways including from blanks. The shank can be made unitarily, integrally with the blade 12 or separately therefrom; and, where fabricated separately, the shank can be attached to the blade in many various ways including brazing and welding. Alignment lines 44 and gauge line 46 can be disposed on blade 12 in many ways, one such way being laser etching. According to a specific embodiment for the knife blade, the linear distance from tip 36 to alignment lines 44 is 0.3 mm and, preferably, 0.33 nun, the linear distance from tip 36 to gauge line 46 is 3.0 mm and the maximum width of the blade is 2.5 mm. In addition to lines, the indicia can include various other types of markings, such as dots or other marks disposed along, adjacent or inwardly of the opposing portions of the cutting edge segments with the dots or marks being aligned in a direction transverse or perpendicular to the axis of the blade. Where the longitudinal axis of blade 12 is disposed at an angle with the longitudinal axis of shank 14 as illustrated in FIG. 4, it is preferred that the axis of the shank be offset 45° from the axis of the blade with an obtuse included angle being defined between the blade and the shank.

Figure 5:
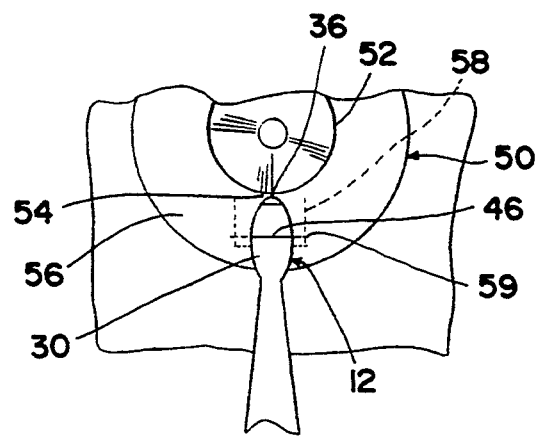
FIG. 5 is a top plan view of an eye to be operated with the tip of the surgical knife blade aligned with an anatomical reference on the eye.
Figure 6:
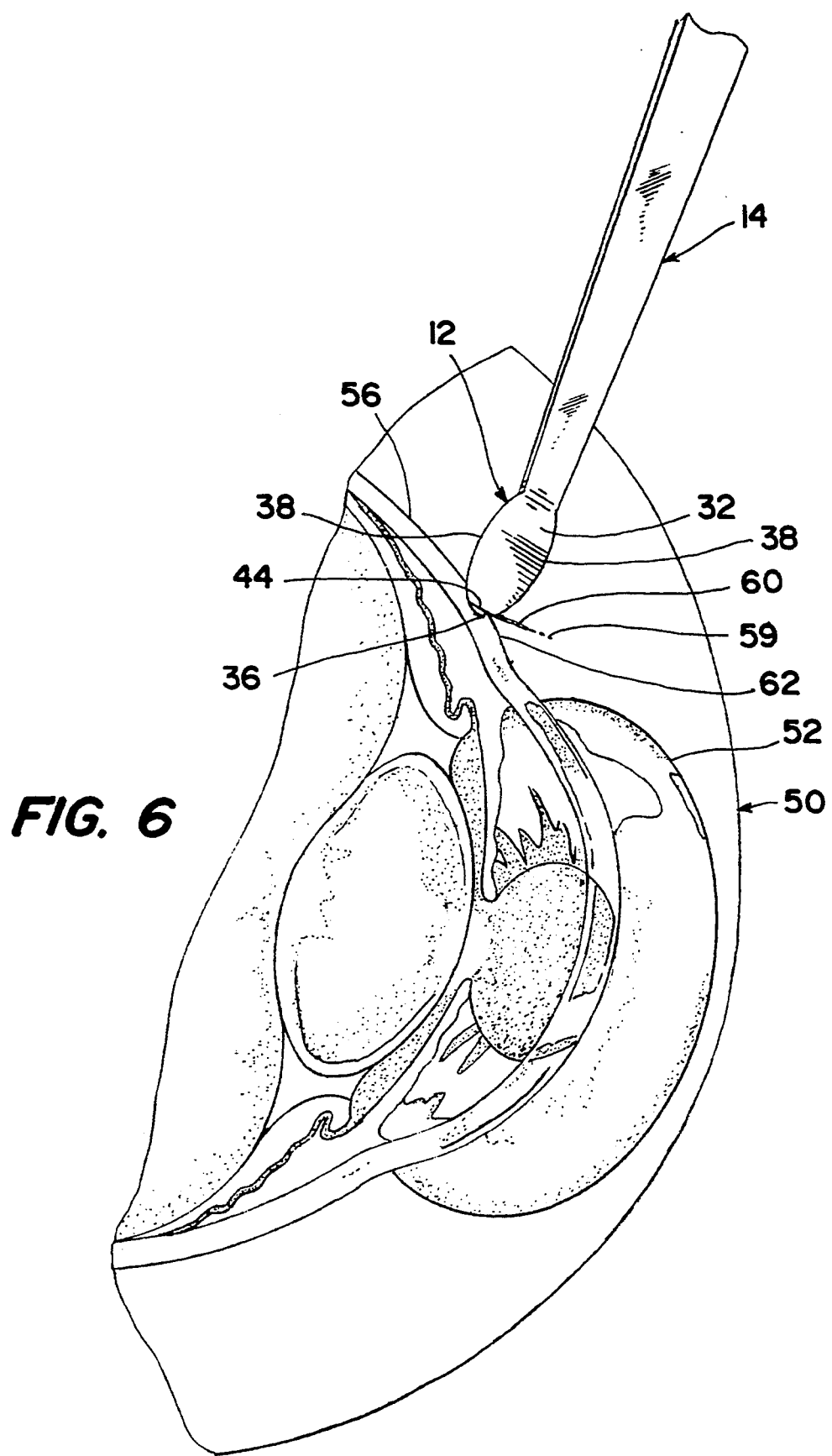
FIG. 6 is a broken perspective view of the eye with the knife blade of FIG. 4 making an initial transverse incision in the sclera of the eye.
Figure 7:
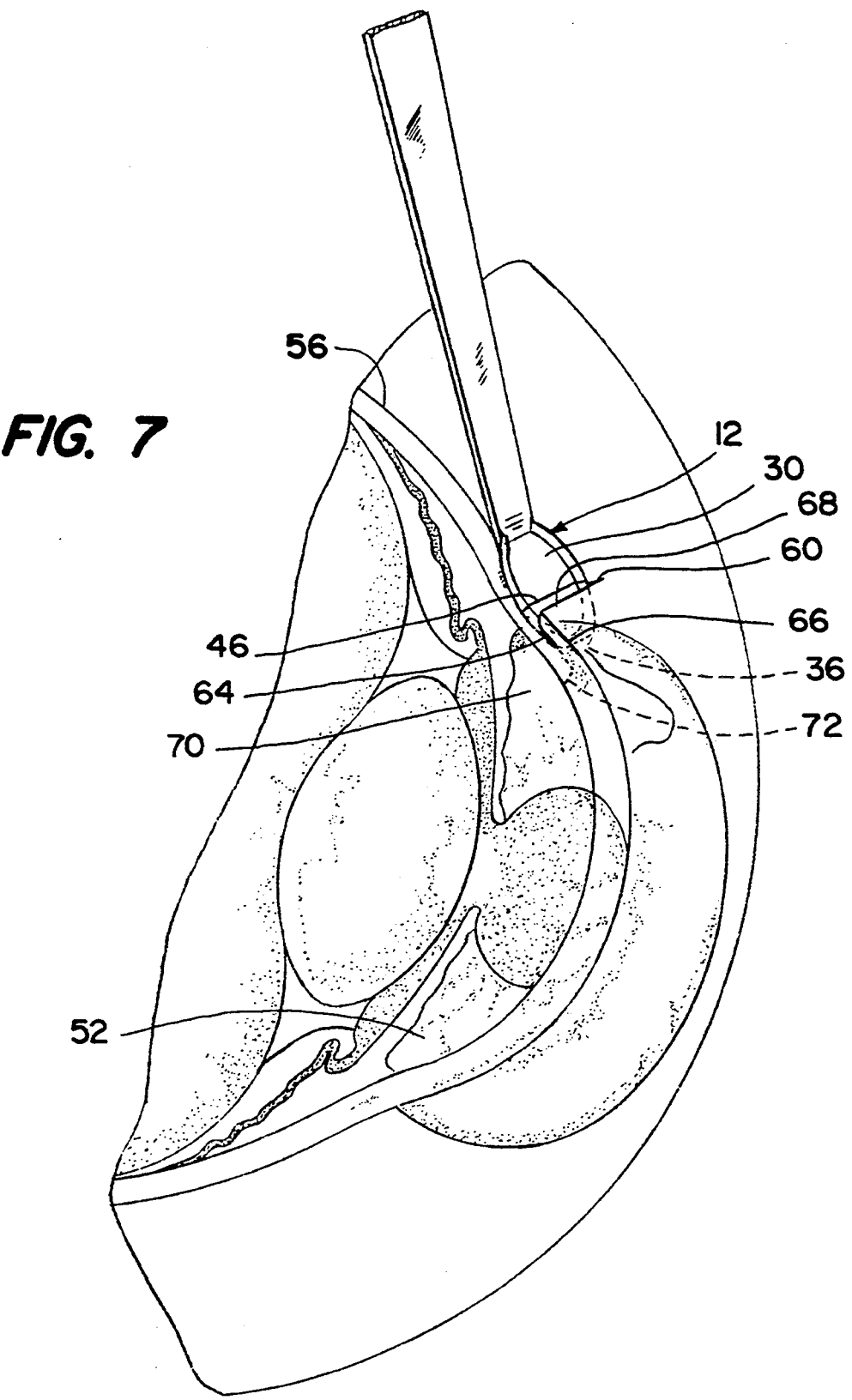
FIG. 7 is a broken perspective view of the eye with the knife blade of FIG. 4 making a subsurface tunnel in the sclera and cornea of the eye.
Figure 8:
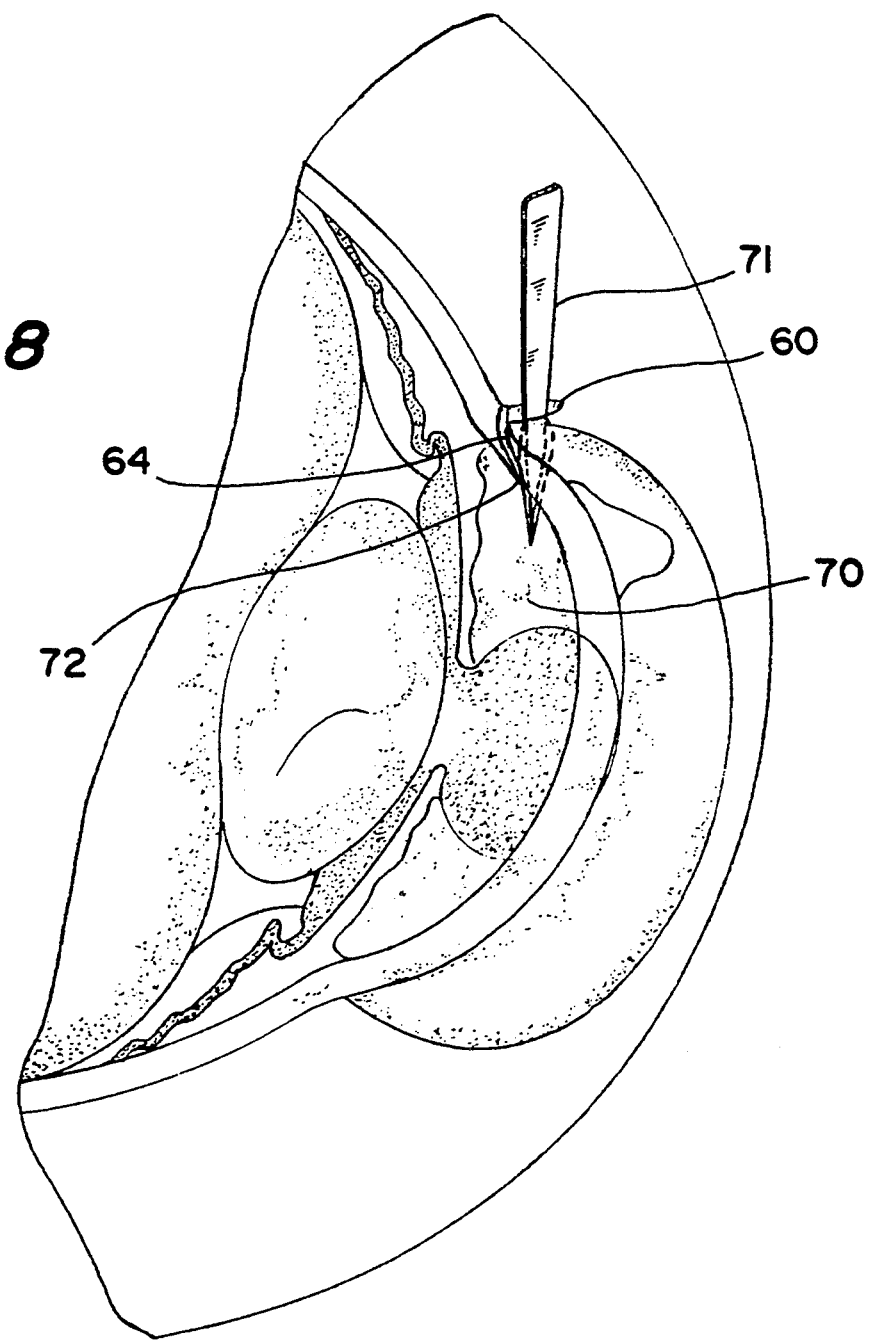
FIG. 8 is a broken perspective view of the eye showing an instrument making a second transverse incision from the subsurface tunnel.

According to a method of operation for the knife blade of the present invention in cataract surgery, an eye 50 to be operated is approached by a surgeon from over the top of the patient's head with the patient lying in a supine position on an operating table, the eye 50 being illustrated in FIG. 5 as viewed by the surgeon from over the forehead or frontal bone of the patient. A 3 mm limbus-based conjunctival flap 5 mm in length is formed by opening and lifting the conjunctiva. Blade 12 is positioned over the eye 50 with anterior surface 30 and gauge line 46 facing the surgeon and the longitudinal axis of the blade extending in a direction radially aligned with iris 52. Tip 36 is aligned with the anterior arcade of vessels 54 of the eye, the anterior arcade of vessels being disposed on the cornea along the circumference thereof at the site of attachment of the conjunctiva to the cornea. The position of gauge line 46 along the sclera 56 of the eye is visually observed to identify the optimal site for an initial horizontal or transverse incision to be made in the eye beneath the previously formed conjunctival flap, the conjunctival flap and the optimal site for the initial scleral incision being shown in broken lines at 58 and 59, respectively, in FIG. 5. Site 59 will be disposed on the sclera a distance posterior to the anterior arcade of vessels that is equal to the linear distance, i.e. 3.0 mm, from tip 36 to gauge line 46 whereat the sclera is 7.5 mm thick. Once site 59 has been established, blade 12 is turned such that posterior surface 32 faces the surgeon, and the blade is inserted in the sclera 56 at site 59 beneath the conjunctival flap 58 in the manner of a plunge cut with the blade inserted tip first into the sclera in a direction normal or transverse thereto to form an initial incision 60 in a plane transverse to the direction radially aligned with iris 52 as illustrated in FIG. 6. Where shank 14 is angularly offset from blade 12 as illustrated in FIG. 6, the bend or angle ensures that the initial incision will be transverse or horizontal to the radially aligned direction. The blade 12 is moved into the sclera along the transverse plane in the direction of insertion until alignment lines 44 are aligned with an external surface 62 of the sclera as illustrated in FIG. 6 and, in particular, until the opposing ends of the alignment lines 44 are aligned with the sclera external surface. Accordingly, tip 36 will be disposed in the sclera a depth less than the thickness of the sclera, such depth being equal to the distance, i.e. 0.30 mm, from tip 36 to alignment lines 44 such that the depth of the initial scleral incision 60 measured from the external surface 62 to a bottom or base of the wound will be 0.30 mm. The depth of the initial scleral incision as determined by alignment lines 44 is important in that, if the initial incision is made deeper, unnecessary bleeding can occur, and the scleral spur can be loosened with displacement of scleral tissue and resultant astigmatism. The blade 12 is moved laterally in a direction aligned with the lateral cutting edge segments 38 until the length of the initial incision 60 is 3.0 mm or otherwise as desired by the surgeon, and the 2.5 mm maximum width of the blade guides the surgeon toward the proper dimensions. Once the initial incision 60 is made to the proper depth and length, blade 12 is withdrawn from the eye and turned such that beveled anterior surface 30 and gauge line 46 are again facing the surgeon as illustrated in FIG. 7. The blade 12 is inserted in the initial incision 60 with tip 36 disposed at the bottom or base thereof and is moved through the thickness of the sclera 56 in the radially aligned direction in a plane transverse or normal to the plane of the initial incision to form a subsurface tunnel 64 having a lower or bottom surface in a plane normal or transverse to the plane of the initial incision 60 as illustrated in FIG. 7. Blade 12 is moved along the tunneling plane in the radially aligned direction to extend the subsurface tunnel into the thickness of the cornea 66; and, accordingly, the subsurface tunnel has a scleral component of length and a corneal component of length. The blade 12 is moved laterally or from side to side with a rotational motion in the tunneling plane such that the width of the subsurface tunnel approximates the length of the initial incision. The length of the subsurface tunnel measured from the initial incision in the radially aligned direction and the extent of commitment into clear cornea is gauged by the surgeon aligning the gauge line 46 with the edge or surface 68 of scleral tissue created by the initial incision 60 transverse to the external tissue surface 62 as illustrated in FIG. 7 wherein the gauge line 46 is shown just prior to alignment with the edge or surface 68. With the gauge line 46 aligned with the edge or surface of scleral tissue, the length of the subsurface tunnel 64 between tip 36 and transverse tissue surface 68 will be 3.0 mm with the tip 36 extending into clear cornea approximately 1.5 mm such that the scleral and corneal components of length are each approximately 1.5 mm in length, the length of the subsurface tunnel being shown partly in broken lines in FIG. 7. Once the commitment into clear cornea has been confirmed, the blade 12 is withdrawn from the eye. As shown in FIG. 8, an instrument, such as a 1 mm keratome 71, for entering the anterior chamber 70 is inserted in the subsurface tunnel 64 via the scleral incision 60, and a second plunge cut incision 72 is made from the bottom of the subsurface tunnel 64 at the closed end thereof through the cornea and into the anterior chamber 70 in a direction transverse or normal to the radially aligned direction such that the second transverse incision 72 is disposed in a plane transverse to the plane of the subsurface tunnel 64 as shown in FIG. 8 and in dotted lines in FIG. 7. An instrument, such as a 3 mm keratome, is inserted in the second transverse incision via the initial and subsurface tunnel incisions and is utilized to enlarge the second incision along the plane thereof. Accordingly, the thusly formed corneal valve incision is a three plane incision made up of the initial transverse incision 60, the subsurface tunnel incision 64 and the second transverse incision 72 with the subsurface tunnel having a scleral component of length and a corneal component of length. The initial and second transverse incisions are formed as plunge cut incisions made in planes transverse to the direction radially aligned with the iris 52 with the subsurface tunnel being made by tunneling in the radially aligned direction along a plane transverse to the planes of the transverse incisions. The planes of the initial and second transverse incisions can be parallel or non-parallel, and the angles formed by the planes of the incisions with the plane of the tunnel can vary dependent on the particular construction for the corneal valve incision. An instrument, such as a phacoemsulifier, for removing a cataractous natural lens is introduced at the anterior chamber through the corneal valve incision. Upon removal of the cataractous natural lens with the instrument, blade 12 is utilized to extend or enlarge the width of the corneal valve incision, where necessary, to accommodate an intraocular lens implant selected to replace the cataractous natural lens, the width typically being increased from the initial 3 mm to approximately 5 mm with the maximum width of the blade guiding the surgeon toward the proper dimensions. The implant is inserted in the eye through the corneal valve incision and is maneuvered into the position previously occupied by the natural lens. The positive pressure of the eye maintains the corneal valve incision closed and the edges of the transverse and tunnel incisions approximated for healing without the need for sutures, and the undisturbed goblet cells in the conjunctival flap ensure a comfortable post-operative period without a foreign body sensation.

A modification of the knife blade according to the present invention is illustrated in FIG. 9 at 110, the knife blade 110 being shown mounted on handle 148. Knife blade 110 is similar to knife blade 10 and includes a shank 114 that is the same as shank 14; however, the configuration of blade 112 for knife blade 110 is different than the configuration of blade 12 for knife blade 10. The end section of shank 114 can be mounted on handle 148 which includes an elongate cylindrical body 174 having external concentric or annular ribs or ridges 176 extending longitudinally therealong to facilitate grasping by a surgeon. The end section can be mounted on handle 148 in many ways including friction fit of the end section in a slot or recess in the handle. Forward section 120 terminates distally at opposing, lateral curved edges 178 joining the shank 114 to blade 112. Blade 112 has opposing, lateral sides or edges 180 symmetrical and parallel with a longitudinal axis of the blade 112 extending longitudinally, distally from edges 178 to cutting edge 134. Cutting edge 134 is made up of opposing, lateral cutting edge segments 138, the cutting edge segments 138 being made up of proximal cutting edge segments 182 and distal cutting edge segments 184. Proximal cutting edge segments 182 are disposed along lateral sides 180 with distal cutting edge segments 184 being angled inwardly from the proximal cutting edge segments in the direction of the longitudinal axis to extend angularly, distally to terminate at tip 136 aligned with the longitudinal axis. Anterior surface 130 is beveled or angled along the lateral cutting edge segments 138 to define a sharp edge with the bevels or angles meeting at ridge 142 aligned with tip 136 and the longitudinal axis. Alignment lines 144 are disposed on the anterior surface 130 and the posterior surface of blade 112 to be disposed 0.30 mm and, preferably, 0.33 mm, from tip 136 as described for blade 10. Gauge line 146 is disposed on the anterior surface 130 to be disposed 3.0 mm from tip 136, the gauge line 146 having opposing ends disposed along opposing portions of sides 180.

Figure 10:
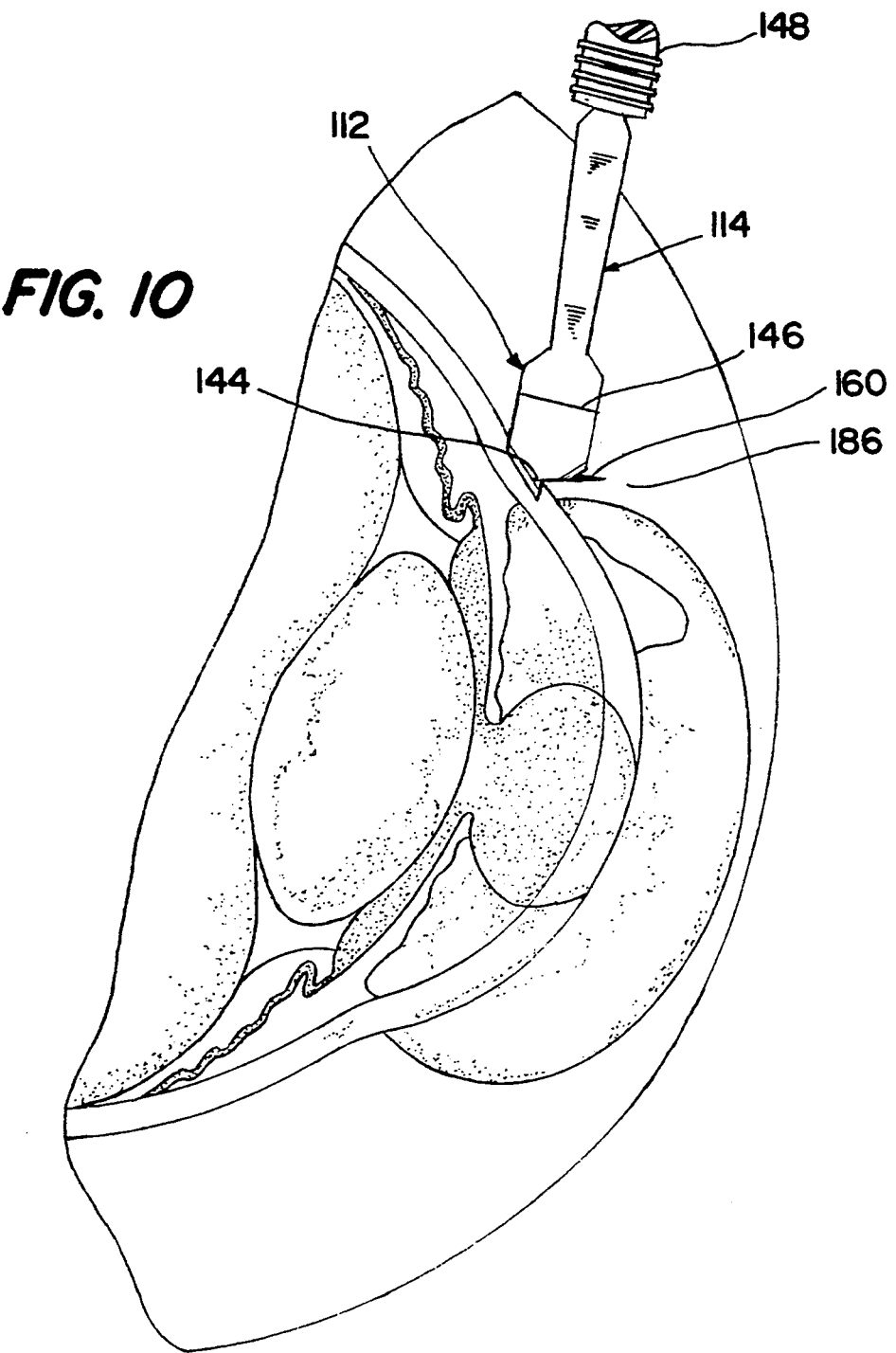
FIG. 10 is a broken perspective view of an eye to be operated with the knife blade of FIG. 9 making an initial transverse incision along the blue line of the limbus of the eye.
Figure 11:
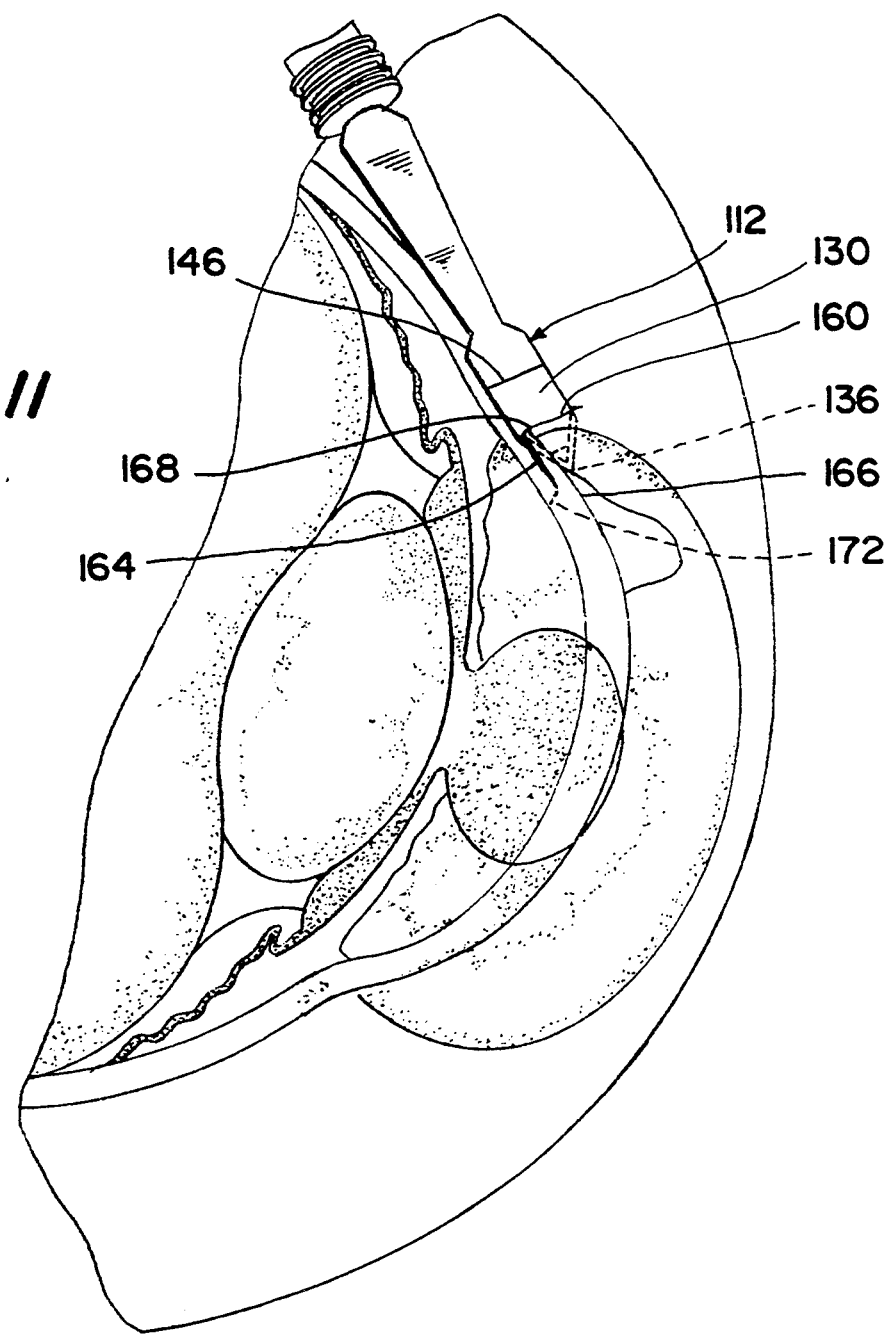
FIG. 11 is a broken perspective view of the eye of FIG. 10 with the knife blade of FIG. 9 making a subsurface tunnel in the cornea of the eye.

Cutting blade 112 is particularly useful in forming a clear-corneal or scleral-less sutureless incision. According to a method of operation for blade 112 in eye surgery, the surgeon makes a 2.3 mm limbus-based conjunctival flap in the eye as previously described for blade 12. Blade 112 is inserted in the tissue of the eye beneath the conjunctival flap at the blue line of the limbus 186 to form an initial transverse incision or groove 160 in the blue line as illustrated in FIG. 10 in a manner similar to that previously described for initial incision 60, the incision 160 being 0.3 mm deep and 3 to 4 mm in length with alignment lines 144 being aligned with an external surface of the tissue at the limbus to control the depth of the initial incision. With gauge line 146 facing the surgeon, the blade is inserted in the initial incision 160 and is moved through the thickness of the cornea 166 to form a subsurface tunnel 164 in a manner similar to that described for subsurface tunnel 64. The blade is moved through the thickness of the cornea 166 until the length of the tunnel is 1.5 mm at which time the blade extends 1.5 mm into clear cornea, the tunnel length and commitment into clear cornea being gauged by aligning the edge 168 of tissue created by the initial incision with the part of anterior surface 130 that is halfway between tip 136 and gauge line 146 as illustrated in FIG. 11. Once the 1.5 mm commitment into clear cornea has been confirmed, blade 112 is withdrawn, and an instrument for entering the anterior chamber is inserted at the closed end of the subsurface tunnel via the initial incision 160. The instrument is utilized to form a second transverse incision, shown in dotted lines at 172, in the same manner as that described for second incision 72. In cataract surgery, an instrument for removing a cataractous natural lens and a selected intraocular lens implant can be inserted through the corneal valve incision which can be enlarged as necessary to accommodate the selected implant, the corneal valve incision typically being enlarged to 4 mm for a foldable intraocular lens implant and 4.50 to 4.75 mm for a biconvex 5 mm round PMMA lens implant.

The instruments and methods for making sutureless incisions according to the present invention provide better maintenance of the anterior chamber of the eye, avoidance of unnecessary bleeding, elimination of postoperative astigmatism, excellent visual results, minimal tissue insult and trauma and simplification of eye surgery and, in particular, cataract surgery. The cutting blades of the present invention can have various configurations to facilitate formation of the transverse incisions and subsurface tunnel. The alignment lines ensure the mandatory 0.3 mm depth for the initial transverse incision to avoid bleeding complications, displacement of scleral tissue and loosening of the scleral spur. The alignment lines being carried on both the anterior and posterior surfaces of the blades facilitates alignment of the lines with the tissue where the initial transverse incision is made with the posterior surfaces of the blades facing the surgeon. The gauge lines permit the site for the initial transverse incision to be optimally located relative to an anatomical reference and the length of the subsurface tunnel and the extent of commitment into cornea to be gauged. The gauge lines can be disposed on the blades at various distances from the tips in accordance with the length of tunnel and commitment into cornea desired. Depending on the location of the gauge lines, the gauge lines can be aligned with the edge of tissue or used as a gauge to judge the distance from the edge of tissue to the tips of the blades to judge tunnel length and commitment into cornea. Where commitment into cornea can be determined by observing the blades through clear cornea, the gauge lines may not be necessary. Depending on the size of the corneal valve incision as formed to allow insertion of an instrument, such as a phacoemulsifier, for removing the cataractous natural lens, the corneal valve incision may not require enlargement prior to inserting the intraocular lens implant. According to the present invention, corneal valve incisions can be constructed with or without a scleral component of length with the tunnel for the scleral-less incision being half the length of the tunnel for the scleral-corneal incision. With entry at the limbus, the clear corneal valve incision provides several additional advantages in patients for whom the clear corneal incision is indicated including elimination of hyphema from the scleral vessels, elimination of the oarlock effect on the tip of the phacoemulsifier and avoidance of scleral spur disinsertion, entry into the anterior chamber too posteriorly at the iris root, cyclodialysis with possible hypotony, release of prostaglandins and iris manipulation with possible miosis.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of making a sutureless incision in eye surgery comprising the steps of
    inserting a knife blade in tissue of the eye along a plane transverse to the tissue to form an initial incision;
    aligning first indicia on the knife blade with an external surface of the tissue to control the depth of a tip of the knife blade in the tissue to obtain a depth for the initial incision that is less than the thickness of the tissue;
    moving the knife blade from the initial incision along a plane transverse to the plane of the initial incision to form a tunnel extending from the initial incision within the thickness of the tissue;
    aligning second indicia on the knife blade relative to an edge of the tissue created by the initial incision to gauge the length of the tunnel from the initial incision; and
    making a second incision from the tunnel through the tissue along a plane transverse to the plane of the tunnel to penetrate through the thickness of the tissue.

2. A method of making a sutureless incision as recited in claim 1 wherein said step of aligning said first indicia includes obtaining a depth of 0.3 mm for the initial incision.

3. A method of making a sutureless incision as recited in claim 2 wherein said step of aligning said second indicia includes gauging the length of the tunnel to be 3.0 mm.

4. A method of making a sutureless incision as recited in claim 3 wherein said step of inserting includes inserting the knife blade with a posterior surface of the knife blade facing the surgeon.

5. A method of making a sutureless incision as recited in claim 4 wherein said step of moving includes moving the knife blade with a beveled anterior surface of the knife blade facing the surgeon.

6. A method of making a sutureless incision as recited in claim 4 wherein said step of making a second incision includes inserting a keratome from the tunnel to penetrate through the thickness of the tissue.

7. A method of making a corneal valve incision in the eye comprising the steps of
   inserting a knife blade in tissue of the eye along a plane transverse to the tissue to form an initial incision;
   aligning first indicia on the knife blade with an external surface of the tissue to obtain a depth for the initial incision that is equal to the distance from the first indicia to a tip of the knife blade;
   moving the knife blade from the initial incision along a plane transverse to the plane of the initial incision in a direction radially aligned with the iris to form a tunnel within the thickness of the cornea;
   aligning second indicia on the knife blade relative to the initial incision to gauge the length of the tunnel; and
   making a second incision from the tunnel through the cornea to complete the corneal valve incision and enter the anterior chamber of the eye.

8. A method of making a corneal valve incision as recited in claim 7 further including, prior to said step of inserting the knife blade, making a conjunctival flap in the eye and wherein said step of inserting the knife blade includes inserting the knife blade in the tissue beneath the conjunctival flap.

9. A method of making a corneal valve incision as recited in claim 4 and further including, prior to said step of inserting the knife blade, the steps of aligning the tip with an anatomical reference on the eye and identifying the location of the second indicia along the tissue to establish a site for the initial incision that is spaced from the anatomical reference a distance equal to the distance from the tip to the second indicia.

10. A method of making a corneal valve incision as recited in claim 9 wherein said step of aligning the tip includes aligning the tip with the anterior arcade of vessels with a longitudinal axis of the blade radially aligned with the iris.

11. A method of making a corneal valve incision as recited in claim 10 wherein said step of inserting the knife blade includes inserting the knife blade in the sclera and said step of moving includes moving the knife blade through the sclera and into the cornea to form a tunnel having a component of length in the sclera and a component of length in the cornea.

12. A method of making a corneal valve incision as recited in claim 8 wherein said step of inserting the knife blade includes inserting the knife blade in the blue line of the limbus of the eye.

* * * * *